United States Patent
Coffindaffer et al.

(10) Patent No.: US 6,627,184 B2
(45) Date of Patent: *Sep. 30, 2003

(54) CONDITIONING SHAMPOO COMPOSITIONS CONTAINING POLYALPHAOLEFIN CONDITIONER

(75) Inventors: Timothy Woodrow Coffindaffer, Loveland, OH (US); Everett Junior Inman, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/348,704

(22) Filed: Jan. 22, 2003

(65) Prior Publication Data

US 2003/0133894 A1 Jul. 17, 2003

Related U.S. Application Data

(63) Continuation of application No. 08/624,922, filed on Mar. 27, 1996, now abandoned.

(51) Int. Cl.$^7$ ............................................. A61K 7/075
(52) U.S. Cl. .................... 424/70.11; 424/70.19; 424/70.21; 424/70.22
(58) Field of Search ............... 424/70.11, 70.19, 424/70.21, 70.22

(56) References Cited

U.S. PATENT DOCUMENTS

| | | |
|---|---|---|
| 2,826,551 A | 3/1958 | Green |
| 3,149,178 A | 9/1964 | Hamilton |
| 3,382,291 A | 5/1968 | Brennan |
| 3,725,498 A | 4/1973 | Brennan |
| 3,964,500 A | 6/1976 | Drakoff |
| 4,073,881 A | 2/1978 | Imai |
| 4,167,486 A | 9/1979 | Rowe |
| 4,175,046 A | 11/1979 | Coant |
| 4,304,678 A | 12/1981 | Schick |
| 4,364,837 A | 12/1982 | Pader |
| 4,524,007 A | 6/1985 | Chibnik |
| 4,555,353 A | 11/1985 | Horodysky |
| 4,587,026 A | 5/1986 | Horodysky |
| 4,657,690 A | 4/1987 | Grollier |
| 4,664,835 A | 5/1987 | Grollier |
| 4,741,855 A | 5/1988 | Grote |
| 4,806,345 A | 2/1989 | Bhattacharyya |
| 4,834,893 A | 5/1989 | Doner |
| 4,967,029 A | 10/1990 | Wu |
| 5,011,681 A | 4/1991 | Ciotti |
| 5,019,282 A | 5/1991 | Farng |
| 5,041,235 A | 8/1991 | Kilburger |
| 5,085,857 A | 2/1992 | Reid |
| 5,105,038 A | 4/1992 | Chen |
| 5,160,739 A | 11/1992 | Kanga |
| 5,221,530 A | 6/1993 | Janchitraponvej |
| 5,302,380 A | 4/1994 | Castrogiovanni |
| 5,338,470 A | 8/1994 | Hiebert |
| 5,417,965 A | 5/1995 | Janchitraponvej |
| 5,449,475 A | 9/1995 | Cavwet et al. |
| 5,573,709 A | 11/1996 | Wells |
| 5,935,561 A * | 8/1999 | Inman et al. ............ 424/70.19 |

FOREIGN PATENT DOCUMENTS

| | | |
|---|---|---|
| AU | 9462606 | 9/1994 |
| EP | 0413416 A2 | 2/1991 |
| EP | 0413417 B1 | 2/1991 |
| EP | 0521665 A1 | 1/1993 |
| EP | 692244 | 1/1996 |
| GB | 849433 | 9/1960 |
| JP | 54-129135 | 10/1979 |
| JP | 56-72095 | 6/1981 |
| JP | 01-168612 | 12/1987 |
| WO | WO-92/10162 | 6/1992 |
| WO | WO-93/08787 A | 5/1993 |
| WO | WO-94/06409 A | 3/1994 |
| WO | WO-97/09031 A | 3/1997 |

* cited by examiner

Primary Examiner—Jyothsan Venkat
(74) Attorney, Agent, or Firm—Brent M. Peebles

(57) ABSTRACT

Disclose are aqueous conditioning shampoo compositions comprising from about 5% to about 50% by weight of an anionic detersive surfactant component selected from the group consisting of anionic surfactants, zwitterionic or amphoteric surfactants having an attached group that is anionic at the pH of the composition, and combinations thereof, from about 0.025% to about 3% by weight of an organic, cationic, hair conditioning polymer, from about 0.05% to about 3% by weight of an organic, water-insoluble, polyalphaolefin conditioning polymer derived from 1-alkene monomers having from about 4 to about 16 carbon atoms, wherein the polyalphaolefin polymer has a viscosity of from about 1 to about 300 centipoise as measured at 40° C.; and from about 20% to about 94% by weight of water. The select polyalphaolefin polymers provide the shampoo composition with improved conditioning performance.

13 Claims, No Drawings

CONDITIONING SHAMPOO COMPOSITIONS CONTAINING POLYALPHAOLEFIN CONDITIONER

CROSS REFERENCE TO RELATED APPLICATION

The application is a continuation of application 08/624,922 filed on Mar. 27, 1996 now abandoned.

FIELD OF THE INVENTION

This invention relates to conditioning shampoo compositions which contain select combinations of hair conditioning agents, and which provide improved hair conditioning performance, including improved wet hair feel.

BACKGROUND OF THE INVENTION

Conditioning shampoos comprising various combinations of detersive surfactant and hair conditioning agents are known. These shampoos have become more popular among consumers as a means of conveniently obtaining hair conditioning and hair cleansing performance all from a single hair care product.

Especially popular among consumers are those conditioning shampoos which comprise a cationic hair conditioning polymer. The cationic polymer provides the shampoo with wet hair conditioning, and in particular helps prevent tangling of hair during and after rinsing, and provides the wet hair with a smooth, silky texture that consumers can associate with optimal conditioning and cleaning performance.

Also popular among consumers are those conditioning shampoos which contain a combination of cationic hair conditioning polymer with other hair conditioning materials. The use of these combined conditioner systems in a shampoo composition provides the consumer with a more balanced hair conditioning profile. Other conditioning agents used in such combinations include silicone conditioning agents to provide improved dry hair conditioning, and organic conditioning oils such as hydrocarbon oils and fatty esters to provide improved wet hair conditioning and softness to the hair when dried. The organic conditioning oils are especially useful when used in combination with a cationic conditioning polymers to provide luster and shine to the hair when dried. These organic conditioning oils, however, are often characterized by consumers as leaving the hair feeling dirty, and causing the hair to appear flat and without fullness and body.

It has now been found that select organic conditioning oils, when used in combination with a cationic conditioning polymer and an anionic detersive surfactant component, provide improved conditioning performance in the form of improved clean hair feel, and improved fullness and body. The select organic conditioning oils are water insoluble, polyalphaolefin polymers derived from 1-alkene monomers having from about 4 to about 14 carbon atoms, wherein the select polyalphaolefin polymers have a viscosity of from about 1 to about 300 centipoise as measured at 40° C.

It is therefore an object of the present invention to provide a hair conditioning shampoo composition with improved hair conditioning performance, and further to provide such a composition with improved hair conditioning performance which also contains a cationic hair conditioning polymer and an organic conditioning oil, and further to provide such a composition which has improved conditioning performance in the form of improved clean hair feel, and improved fullness and body.

SUMMARY OF THE INVENTION

The present invention is directed to hair conditioning shampoo compositions which comprise (A) from about 5% to about 50% by weight of an anionic detersive surfactant component selected from the group consisting of anionic surfactants, zwitterionic or amphoteric surfactants having an attached group that is anionic at the pH of the composition, and combinations thereof, (B) from about 0.025% to about 3% by weight of an organic, cationic, hair conditioning polymer, (C) from about 0.05% to about 3% by weight of an organic, water-insoluble, polyalphaolefin polymer derived from 1-alkene monomers having from about 4 to about 14 carbon atoms, wherein the polyalphaolefin has a viscosity of from about 1 to about 300 centipoise as measured at 40° C; and (D) from about 20% to about 94% by weight of water. The select polyalphaolefins provide the composition with improved conditioning performance.

DETAILED DESCRIPTION OF THE INVENTION

The shampoo compositions of the present invention can comprise, consist of, or consist essentially of the essential elements and limitations of the invention described herein, as well any of the additional or optional ingredients, components, or limitations described herein.

All percentages, parts and ratios are based on the total weight of the shampoo compositions of the present invention, unless otherwise specified. All such weights as they pertain to listed ingredients are based on the active level and, therefore, do not include carriers or by-products that may be included in commercially available materials, unless otherwise specified.

As used herein, the term "soluble" refers to materials that are sufficiently soluble in water to form a substantially clear solution to the naked eye at a concentration of 0.1% by weight of the material in water at 25° C. Conversely, the term "insoluble" refers to all other materials that are therefore not sufficiently soluble in water to form a substantially clear solution to the naked eye at a concentration of 0.1% by weight of the other material in water at 25° C.

As used herein, the term "low viscosity" refers to viscosity of from about 1 to about 300 centipoise, preferably from about 1 to about 150 centipoise, more preferably from about 2 to about 50 centipoise. All viscosity values herein are measured at a temperature of 40° C by the ASTM D-445 method.

As used herein, "nonvolatile" refers to any material having little or no significant vapor pressure under ambient conditions, and a boiling point under one atmosphere (atm) preferably at least about 250° C. The vapor pressure under such conditions is preferably less than about 0.2 mm Hg at 25° C. or less, preferably less than about 0.1 mm Hg at 25° C. or less.

As used herein, the term "liquid" refers to any visibly (by the naked eye) flowable fluid under ambient conditions (about 1 atmosphere of pressure at about 25° C.)

The shampoo compositions of the present invention including the essential and some optional components thereof, are described in detail hereinafter.

Anionic Detersive Surfactant Component

The shampoo compositions of the present invention comprise an anionic detersive surfactant component to provide cleaning performance to the composition. The anionic detersive surfactant component in turn comprises anionic detersive surfactant, zwitterionic or amphoteric detersive surfactant which has an attached group that is anionic at the pH of the composition, or a combination thereof, preferably anionic detersive surfactant. Such surfactants should be physically and chemically compatible with the essential components described herein, or should not otherwise unduly impair product stability, aesthetics or performance.

Suitable anionic detersive surfactant components for use in the shampoo composition herein include those which are known for use in hair care or other personal care cleansing compositions. The concentration of the anionic surfactant component in the shampoo composition should be sufficient to provide the desired cleaning and lather performance, and generally range from about 5% to about 50%, preferably from about 8% to about 30%, more preferably from about 10% to about 25%, even more preferably from about 12% to about 18%, by weight of the composition.

Preferred anionic surfactants suitable for use in the shampoo compositions are the alkyl and alkyl ether sulfates. These materials have the respective formulae $ROSO_3M$ and $RO(C_2H_4O)_xSO_3M$, wherein R is alkyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium. The cation M should be selected such that the anionic detersive surfactant component is water soluble. Solubility of the surfactant will depend upon the particular anionic detersive surfactants and cations chosen.

Preferably, R has from about 8 to about 18 carbon atoms, more preferably from about 10 to about 16 carbon atoms, even more preferably from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, preferably from about 2 to about 5, more preferably about 3, molar proportions of ethylene oxide, and the resulting mixture of molecular species having, for example, an average of 3 moles of ethylene oxide per mole of alcohol, is sulfated and neutralized.

Specific non limiting examples of alkyl ether sulfates which may be used in the shampoo compositions of the present invention include sodium and ammonium salts of coconut alkyl triethylene glycol ether sulfate, tallow alkyl triethylene glycol ether sulfate, and tallow alkyl hexaoxyethylene sulfate. Highly preferred alkyl ether sulfates are those comprising a mixture of individual compounds, wherein the compounds in the mixture have an average alkyl chain length of from about 10 to about 16 carbon atoms and an average degree of ethoxylation of from about 1 to about 4 moles of ethylene oxide.

Other suitable anionic detersive surfactants are the water-soluble salts of organic, sulfuric acid reaction products conforming to the formula $[R^1—SO_3—M]$ where $R^1$ is a straight or branched chain, saturated, aliphatic hydrocarbon radical having from about 8 to about 24, preferably about 10 to about 18, carbon atoms; and M is a cation described hereinbefore. Non limiting examples of such detersive surfactants are the salts of an organic sulfuric acid reaction product of a hydrocarbon of the methane series, including iso-, neo-, and n-paraffins, having from about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10}$ to $C_{18}$ n-paraffins.

Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. No. 2,486,921; U.S. Pat. No. 2,486,922; and U.S. Pat. No. 2,396,278, which descriptions are incorporated herein by reference.

Other anionic detersive surfactants suitable for use in the shampoo compositions are the succinnates, examples of which include disodium N-octadecylsulfosuccinnate; disodium lauryl sulfosuccinate; diammonium lauryl sulfosuccinate; tetrasodium N-(1,2-carboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic detersive surfactants include olefin sulfonates having about 10 to about 24 carbon atoms. In this context the term "olefin sulfonates" refers to compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form. The alpha-olefins from which the olefin sulfonates are derived are mono-olefins having from about 10 to about 24 carbon atoms, preferably from about 12 to about 16 carbon atoms. Preferably, they are straight chain olefins. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880, which description is incorporated herein by reference.

Another class of anionic detersive surfactants suitable for use in the shampoo compositions are the beta-alkyloxy alkane sulfonates. These surfactants conform to the formula

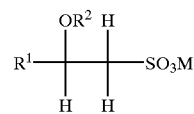

where $R^1$ is a straight chain alkyl group having from about 6 to about 20 carbon atoms, $R^2$ is a lower alkyl group having from about 1 to about 3 carbon atoms, preferably 1 carbon atom, and M is a water-soluble cation as described hereinbefore.

Preferred anionic detersive surfactants for use in the shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, arumonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

Suitable amphoteric or zwitterionic detersive surfactants for use in the shampoo composition herein include those which are known for use in hair care or other personal care cleansing composition, and which contain a group that is anionic at the pH of the shampoo composition. Concentration of such amphoteric detersive surfactants preferably ranges from about 0.5% to about 20%, preferably from about 1% to about 10%, by weight of the composition. Non limiting examples of suitable zwitterionic or amphoteric surfactants are described in U.S. Pat. No. 5,104,646 (Bolich Jr. et al.), U.S. Pat. No. 5,106,609 (Bolich Jr. et al.), which descriptions are incorporated herein by reference.

Amphoteric detersive surfactants suitable for use in the shampoo composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate.

Zwitterionic detersive surfactants suitable for use in the shampoo composition are well known in the art, and include those surfactants broadly described as derivatives of aliphatic quaternary amimonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred.

The shampoo compositions of the present invention may further comprise additional surfactants for use in combination with the anionic detersive surfactant component described hereinbefore. Suitable optional surfactants include nonionic surfactants, cationic surfactants, and combinations thereof. Any such surfactant known in the art for use in hair or personal care products may be used, provided that the optional additional surfactant is also chemically and physically compatible with the essential components of the shampoo composition, or does not otherwise unduly impair product performance, aesthetics or stability. The concentration of the optional additional surfactants in the shampoo composition may vary with the cleansing or lather performance desired, the optional surfactant selected, the desired product concentration, the presence of other components in the composition, and other factors well known in the art Non limiting examples of other anionic, zwitterionic, amphoteric or optional additional surfactants suitable for use in the shampoo compositions are described in McCutcheon's. Emulsifiers and Detergents. 1989 Annual, published by M. C. Publishing Co., and U.S. Pat. No. 3,929,678, U.S. Pat. No. 2,658,072; U.S. Pat. No. 2,438,091; U.S. Pat. No. 2,528,378, which descriptions are incorporated herein by reference.

Cationic Hair Conditioning Polymer

The shampoo compositions of the present invention comprise an organic, cationic polymer as a hair conditioning agent. Suitable polymers are those known cationic polymers that provide conditioning benefits to hair. Such cationic polymers should also be physically and chemically compatible with the essential components described herein, or should not otherwise unduly impair product stability, aesthetics or performance.

The concentration of the organic, cationic, conditioning polymer of the shampoo composition should be sufficient to provide the desired conditioning benefits. Such concentrations generally range from about 0.025% to about 3%, preferably from about 0.05% to about 2%, more preferably from about 0.1% to about 1%, by weight of the shampoo composition.

The cationic conditioning polymer contains cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the shampoo composition. The average molecular weight of the cationic conditioning polymers is between about 10 million and about 5,000, preferably at least about 100,000, more preferably at least about 200,000, but preferably not more than about 2 million, preferably not more than about 1.5 million. The polymers also have a cationic charge density ranging from about 0.2 meq/gm to about 7 meq/gm, preferably at least about 0.4 meq/gm, more preferably at least about 0.6 meq/gm, but also preferably less than about 5 meq/gm, more preferably less than about 2 meq/gm, at the pH of intended use of the shampoo composition, which pH will generally range from about pH 3 to about pH 9, preferably between about pH 4 and about pH7.

Any anionic counterions can be use in association with the cationic conditioning polymers so long as the polymers remain soluble in water, in the shampoo composition, or in a coacervate phase of the shampoo composition, and so long as the counterions are physically and chemically compatible with the essential components of the shampoo composition or do not otherwise unduly impair product performance, stability or aesthetics. Non limiting examples of such counterions include halides (e.g., chlorine, fluorine, bromine, iodine), sulfate and methylsulfate.

The cationic nitrogen-containing moiety of the cationic polymer is generally present as a substituent on all, or more typically on some, of the monomer units thereof Thus, the cationic polymer for use in the shampoo composition includes homopolymers, copolymers, terpolymers, and so forth, of quaternary ammonium or cationic amine-substituted monomer units, optionally in combination with non-cationic monomers referred to herein as spacer monomers. Non limiting examples of such polymers are described in the *CTFA Cosmetic Ingredient Dictionary*, 3rd edition, edited by Estrin Crosley, and Haynes, (The Cosmetic, Toiletry, and Fragrance Association, Inc., Washington, D.C. (1982), which description is incorporated herein by reference.

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone. The alkyl and dialkyl substituted monomers preferably have from $C_1$ to $C_7$ alkyl grows, more preferably from $C_1$ to $C_3$ alkyl groups. Other suitable spacer monomers include vinyl esters, vinyl alcohol (made by hydrolysis of polyvinyl acetate), maleic anhydride, propylene glycol, and ethylene glycol.

Suitable cationic protonated amino and quaternary ammonium monomers, for inclusion in the cationic polymers of the shampoo composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$, $C_2$ or $C_3$ alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

Other suitable cationic polymers for use in the shampoo composition include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., U.S.A.) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from ISP Corporation (Wayne, N.J., U.S.A.) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homopolymers and copolymers of unsaturated carboxylic acids having from 3 to 5 carbon atoms, as described in U.S. Pat. No. 4,009,256, which description is incorporated herein by reference.

Other suitable cationic polymers for use in the shampoo composition include polysaccharide polymers, such as cationic cellulose derivatives and cationic starch derivatives. Suitable cationic polysaccharide polymers include those which conform to the formula

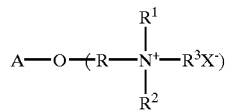

wherein A is an anhydroglucose residual group, such as a starch or cellulose anhydroglucose residual; R is an alkylene oxyalkylene, polyoxyalkylene, or hydroxyalkylene group, or combination thereof, R1, R2, and R3 independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in R1, R2 and R3) preferably being about 20 or less; and X is an anionic counterion as described in hereinbefore.

Preferred cationic cellulose polymers are those polymers available from Amerchol Corp. (Edison, N.J., USA) in their Polymer JR and LR series of polymers, as salts of hydroxyethyl cellulose reacted with trimethyl ammonium substituted epoxide, referred to in the industry (CTFA) as Polyquaternium 10. Another type of preferred cationic cellulose includes the polymeric quaternary ammonium salts of hydroxyethyl cellulose reacted with lauryl dimethyl ammonium-substituted opoxide, referred to in the industry (CTFA) as Polyquaternium 24. These materials are available from Amerchol Corp. (Edison, N.J., USA) under the trade name Polymer LM-200.

Other suitable cationic polymers include cationic guar gum derivatives, such as guar hydroxypropyltrimonium chloride, specific examples of which include the Jaguar series commercially available from Celanese Corporation. Other suitable cationic polymers include quaternary nitrogen-containing cellulose ethers, some examples of which are described in U.S. Pat. No. 3,962,418, which description is incorporated herein by reference herein. Other suitable cationic polymers include copolymers of etherified cellulose, guar and starch, some examples of which are described in U.S. Pat. No. 3,958,581, which description is incorporated herein by reference.

The organic, cationic hair conditioning polymers herein are either soluble in the shampoo composition, or preferably are soluble in a complex coacervate phase in the shampoo composition formed by the cationic polymer and the anionic detersive surfactant component described hereinbefore. Complex coacervates of the cationic polymer can also be formed with other optional anionic components of the shampoo composition.

Coacervate formation is dependent upon a variety of criteria such as molecular weight, component concentration, and ratio of interacting ionic components, ionic strength (including modification of ionic strength, for example, by addition of salts), charge density of the cationic and anionic components, pH, and temperature. Coacervate systems and the effect of these parameters have been described, for example, by J. Caelles, et al., "Anionic and Cationic Compounds in Mixed Systems", *Cosmetics & Toiletries*, Vol. 106, April 1991, pp 49–54, C. J. van Oss, "Coacervation, Complex-Coacervation and Flocculation", *J. Dispersion Science and Technology*, Vol. 9 (5,6), 1988–89, pp 561–573, and D. J. Burgess, "Practical Analysis of Complex Coacervate Systems", *J. of Colloid and Interface Science*, Vol. 140, No. 1, November 1990, pp 227–238, which descriptions are incorporated herein by reference.

It is believed to be particularly advantageous for the cationic polymer to be present in the shampoo composition in a coacervate phase, or to form a coacervate phase upon application or rinsing of the shampoo to or from the hair. Complex coacervates are believed to more readily deposit on the hair. Thus, in general, it is preferred that the cationic polymer exist in the shampoo composition as a coacervate phase or form a coacervate phase upon dilution. If not already a coacervate in the shampoo composition, the cationic polymer will preferably exist in a complex coacervate form in the shampoo upon dilution with water.

Techniques for analysis of formation of complex coacervates are known in the art. For example, microscopic analyses of the shampoo compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the shampoo composition.

Polyalphaolefin Conditioning Oil

The shampoo compositions of the present invention comprise select polyalphaolefin polymers as an organic conditioning oil for use in combination with the cationic hair conditioning polymer described hereinbefore. The concentration of the select polymers ranges from about 0.05% to about 3%/o, preferably from about 0.08% to about 1.5%, more preferably from about 0.1% to about 1%, by weight of the shampoo composition.

The select polyalphaolefin polymers for use in the shampoo composition are water insoluble, organic, water dispersible, polyalphaolefin polymers having a viscosity of from about 1 to about 300 centipoise, preferably from about 1 to about 150 centipoise, more preferably from about 2 to about 50 centipoise, as measured at 40° C. These select polymers are derived from 1-alkene monomers having from about 4 to about 16 carbon atoms, preferably from about 6 to about 12 carbon atoms, more preferably from about 8 to about 12. The select polymers are preferably hydrodgenated polyalphaolefin polymers.

Non limiting examples of 1-alkene monomers for use in preparing the select polyalphaolefin polymers herein include 1-butene, 1-pentene, 1-hexene, 1-octene, 1-decene, 1-dodecene, 1-tetradecene, branched chain isomers such as 4-methyl-1-pentene, and combinations thereof. Also suitable for preparing the polyolefin liquids are olefin-containing refinery feedstocks or effluents.

Preferred, 1-alkene monomers are 1-hexene to 1-hexadecenes and combinations thereof, more preferably -1octene to 1-dodecene, or combinations thereof.

Water

The shampoo compositions of the present invention arc aqueous systems which comprise from about 20% to about 94%, preferably from about 50% to about 90%, more preferably from about 60% to about 85%, water by weight of the composition.

Optional Components

The shampoo compositions of the present invention may further comprise one or more optional components known for use in hair care or personal care products, provided that the optional components are physically and chemically compatible with the essential component described herein, or do not otherwise unduly impair product stability, aesthetics or performance. Concentrations of such optional components typically and individually range from about 0.001% to about 10% by weight of the shampoo compositions.

Non limiting examples of optional components for use in the shampoo composition include anti static agents, anti dandruff agents, conditioning agents (additional hydrocarbon oils, fatty esters, silicone), dyes, organic solvents or diluents, pearlescent aids, foam boosters, additional surfactants or cosurfactants (nonionic, cationic), pediculocides, pH adjusting agents, perfumes, preservatives, proteins, skin active agents, styling polymers, sunscreens, vitamins, and viscosity adjusting agents.

The shampoo composition of the present invention preferably further comprises a suspending or thickening agent. Suitable suspending agents for such materials are well known in the art, and include crystalline and polymeric suspending or thickening agents. Crystalline suspending agents are preferred, and include known acyl derivatives and amine oxides, and are described in U.S. Pat. No. 4,741,855, which description is incorporated herein by reference.

Non limiting examples of optional polymeric thickening agents for use in the shampoo composition include carboxyvinyl polymers, cellulose ethers, guar gum, polyvinyl alcohol, polyvinyl pyrrolidone, hydroxypropyl guar gum, starch and starch derivatives, and xantham gum. Suspending or thickening agents are described in U.S. Pat. No. 2,798,053, U.S. Pat. No. 4,686,254, U.S. Pat. No. 4,788,006, and U.S. Pat. No. 5,275,761, which descriptions are incorporated herein by reference. The optional suspending or thickening agents are described in more detail hereinafter.

The shampoo compositions of the present invention also preferably comprises a silicone hair conditioning agent, more preferably a silicone hair conditioning agent in combination with an optional suspending agent for the silicone. The silicone hair conditioning agent is preferably non volatile, and is preferably present in the shampoo composition at concentrations ranging from about 0.01% to about 10%, by weight of the shampoo composition. Non limiting examples of suitable silicone hair conditioning agents, and optional suspending agents for the silicone, are described in U.S. Reissue Pat. No. 34,584 (Grote et al.), U.S. Pat. No. 5,104,646 (Bolich Jr. et al.), U.S. Pat. No. 5,106,609 (Bolich Jr. et al.), which descriptions are incorporated herein by reference. The optional silicone hair conditioning agent, and optional suspending agents for the optional silicone, are described in more detail hereinafter Optional Silicone Hair Conditioning Agent The shampoo compositions of the present invention may further comprise an optional silicone hair conditioning agent at concentrations effective to provide hair conditioning benefits. Such concentrations range from about 0.01% to about 10%, preferably from about 0.1% to about 8%, more preferably from about 0.1% to about 5%, most preferably from about 0.2% to about 3%, by weight of the shampoo compositions.

The optional silicone hair conditioning agents are insoluble in the shampoo compositions, and are preferably nonvolatile. Typically it will be intermixed in the shampoo composition so as to be in the form of a separate, discontinuous phase of dispersed, insoluble particles, also referred to as droplets. These droplets are typically suspended with an optional suspending agent described hereinafter. The optional silicone hair conditioning agent phase will comprise a silicone fluid hair conditioning agent such as a silicone fluid and can also comprise other ingredients, such as a silicone resin to improve silicone fluid deposition efficiency or enhance glossiness of the hair (especially when high refractive index (e.g. above about 1.46) silicone conditioning agents are used (e.g. highly phenylated silicones).

The optional silicone hair conditioning agent phase may comprise volatile silicone, nonvolatile silicone, or combinations thereof. Typically, if volatile silicones are present, it will be incidental to their use as a solvent or carrier for commercially available forms of nonvolatile silicone materials ingredients, such as silicone gums and resins.

The optional silicone hair conditioning agents for use in the shampoo compositions preferably have a viscosity of from about 20 to about 2,000,000 centistokes, more preferably from about 1,000 to about 1,800,000 centistokes, even more preferably from about 50,000 to about 1,500,000 centistokes, most preferably from about 100,000 to about 1,500,000 centistokes, as measured at 25° C.

Optional silicone fluids include silicone oils which are flowable silicone materials having a a viscosity of less than 1,000,000 centistokes, preferably between about 5 and 1,000,000 centistokes, more preferably between about 10 and about 100,000 centistokes, at 25° C. Suitable silicone oils include polyalkyl siloxanes, polyaryl siloxanes, polyalkylaryl siloxanes, polyether siloxane copolymers, and combinations thereof. Other insoluble, nonvolatile silicone fluids having hair conditioning properties can also be used.

Optional silicone oils include polyalkyl or polyaryl siloxanes which conform to the following formula (I)

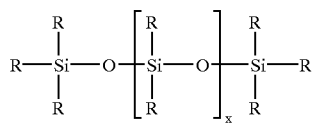

where R is aliphatic, preferably alkyl or alkenyl, or aryl, R can be substituted or unsubstituted, and x is an integer from 1 to about 8,000. Suitable unsubstituted R groups include alkoxy, aryloxy, alkaryl, arylalkyl, arylalkenyl, alkamnino, and ether-substituted, hydroxyl-substituted, and halogen-substituted aliphatic and aryl groups. Suitable R groups also include cationic amines and quaternary ammonium groups.

The aliphatic or aryl groups substituted on the siloxane chain may have any structure so long as the resulting silicones remain fluid at room temperature, are hydrophobic, are neither irritating, toxic nor otherwise harmful when applied to the hair, are compatible with the other components of the shampoo compositions, are chemically stable under normal use and storage conditions, are insoluble in the shampoo compositions herein, and are capable of being deposited on and conditioning the hair.

The two R groups on the silicon atom of each monomeric silicone unit may represent the same or different groups. Preferably, the two R groups represent the same group.

Preferred alkyl and alkenyl substituents are $C_1$–$C_5$ alkyls and alkenyls, more preferably from $C_1$–$C_4$, most preferably from $C_1$–$C_2$. The aliphatic portions of other alkyl-, alkenyl-, or alkynyl-containing groups (such as alkoxy, alkaryl, and alkamino) can be straight or branched chains and preferably have from one to five carbon atoms, more preferably from one to four carbon atoms, even more preferably from one to three carbon atoms, most preferably from one to two carbon atoms. As discussed above, the R substituents hereof can also contain amino functionalities, e.g. alkamino groups, which can be primary, secondary or tertiary amines or quaternary ammonium These include mono-, di- and tri-alkylamino and alkoxyamino groups wherein the aliphatic portion chain length is preferably as described above. The R substituents can also be substituted with other groups, such as halogens (e.g. chloride, fluoride, and bromide), halogenated aliphatic or aryl groups, and hydroxy (e.g. hydroxy substituted aliphatic groups). Suitable halogenated R groups could include, for example, tri-halogenated (preferably fluoro) alkyl groups such as —$R^1$—$C(F)_3$, wherein $R^1$ is $C_1$–$C_3$ alkyl. Examples of such polysiloxanes include polymethyl -3,3,3trifluoropropylsiloxane.

Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred. Other suitable R groups include methyl, methoxy, ethoxy, propoxy, and aryloxy. The three R groups on the end caps of the silicone may also represent the same or different groups.

The nonvolatile polyalkylsiloxane fluids that may be used include, for example, polydimethylsiloxanes. These siloxanes are available, for example, from the General Electric Company in their Viscasil R and SF 96 series, and from Dow Corning in their Dow Corning 200 series.

The polyalkylaryl siloxane fluids that may be used, also include, for example, poymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide concentrations must be sufficiently low to prevent solubility in water and the composition hereof.

Suitable alkylamino substituted silicones include those which conform to the following structure (II)

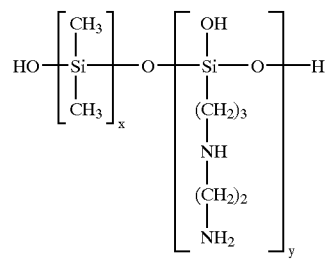

wherein x and y are integers. This polymer is also known as "amodimethicone".

Suitable cationic silicone fluids include those which conform to the formula (III) $(R_1)_a G_{3-a}$—Si—$(-OSiG_2)_n$—$(-SiG_b(R_1)_{2-b})_m$—O—$SiG_{3-a}(R_1)_a$, wherein G is selected from the group consisting of hydrogen phenyl, hydroxy, $C_1$–$C_8$ alkyl and preferably methyl; a is 0 or an integer having a value from 1 to 3, preferably 0; b is 0 or 1, preferably 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10; $R^1$ is a monovalent radical conforming to the formula $CqH_{2q}L$ in which q is an integer having a value of from 2 to 8 and L is selected from the following groups:

—$N(R_2)CH_2$—$CH_2$—$N(R_2)_2$
—$N(R_2)_2$
—$N(R_2)_3 A^-$
—$N(R_2)CH_2$—$CH_2$—$NR_2H_2 A^-$ in which $R_2$ is selected from the group consisting of hydrogen, phenyl, benzyl, a saturated hydrocarbon radical, preferably an alkyl radical containing from 1 to 20 carbon atoms, and $A^-$ is a halide ion.

An especially preferred cationic silicone corresponding to formula (III) is the polymer known as "trimethylsilylamodimethicone", of formula (IV):

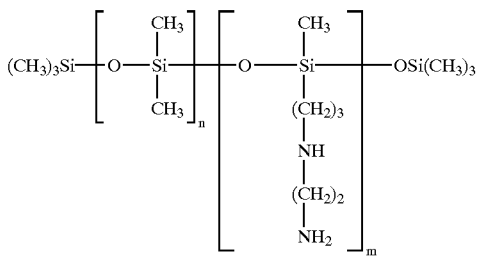

Other silicone cationic polymers which can be used in the shampoo compositions are represented by the formula (V):

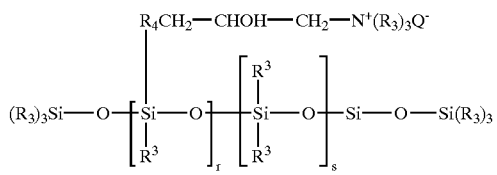

where $R^3$ denotes a monovalent hydrocarbon radical having from 1 to 18 carbon atoms, preferably an alkyl or alkenyl radical such as methyl; $R_4$ denotes a hydrocarbon radical, preferably a $C_1$–$C_{18}$ alkylene radical or a $C_1$–$C_{18}$, and more preferably $C_1$–$C_8$, alkyleneoxy radical; $Q^-$ is a halide ion, preferably chloride; r denotes an average statistical value from 2 to 20, preferably from 2 to 8; s denotes an average statistical value from 20 to 200, and preferably from 20 to 50. A preferred polymer of this class is available from Union Carbide under the name "UCARE SILICONE ALE 56."

Other optional silicone fluids are the insoluble silicone gums. These gums are polyorganosiloxane materials having a viscosity at 25° C. of greater than or equal to 1,000,000 centistokes. Silicone gums are described in U.S. Pat. No. 4,152,416; Noll and Walter, *Chemistry and Technology of Silicones*. New York: Academic Press 1968; and in General Electric Silicone Rubber Product Data Sheets SE 30, SE 33, SE 54 and SE 76, all of which are incorporated herein by reference. The silicone gums will typically have a mass molecular weight in excess of about 200,000, generally between about 200,000 and about 1,000,000, specific examples of which include polydimethylsiloxane, (polydimethylsiloxane) (methylvinylsiloxane) copolymer, poly(dimethylsiloxane) (diphenyl siloxane) (methylvinylsiloxane) copolymer and mixtures thereof.

Another category of nonvolatile, insoluble silicone fluid conditioning agents are the high refractive index silicones, having a refractive index of at least about 1.46, preferably at least about 1.48, more preferably at least about 1.52, most preferably at least about 1.55. The refractive index of the polysiloxane fluid will generally be less than about 1.70, typically less than about 1.60. In this context, polysiloxane "fluid" includes oils as well as gums.

The high refractive index polysiloxane fluid includes those represented by general Formula (I) above, as well as cyclic polysiloxanes such as those represented by Formula (VI) below:

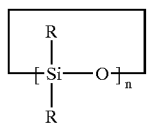

wherein R is as defined above, n is from about 3 to about 7, preferably from 3 to 5.

The high refractive index polysiloxane fluids contain a sufficient amount of aryl-containing R substituents to increase the refractive index to the desired level, which is described above. In addition, R and n must be selected so that the material is nonvolatile, as defined above.

Aryl-containing substituents contain alicyclic and heterocyclic five and six membered aryl rings, and substituents containing fused five or six membered rings. The aryl rings themselves can be substituted or unsubstituted. Substituents include aliphatic substituents, and can also include alkoxy substituents, acyl substituents, ketones, halogens (e.g., Cl and Br), amines, etc. Exemplary aryl-containing groups include substituted and unsubstituted arenes, such as phenyl, and phenyl derivatives such as phenyls with $C_1$–$C_5$ alkyl or alkenyl substituents, e.g., allylphenyl, methyl phenyl and ethyl phenyl, vinyl phenyls such as styrenyl, and phenyl alkynes (e.g. phenyl $C_2$–$C_4$ alkynes). Heterocyclic aryl groups include substituents derived from ran, imidazole, pyrrole, pyridine, etc. Fused aryl ring substituents include, for example, napthalene, coumarin, and purine.

In general, the high refractive index polysiloxane fluids will have a degree of aryl-containing substituents of at least about 150%, preferably at least about 20%, more preferably at least about 25%, even more preferably at least about 35%, most preferably at least about 50%. Typically, although it is not intended to necessarily limit the invention, the degree of aryl substitution will be less than about 90%, more generally less than about 85%, preferably from about 55% to about 80%.

The polysiloxane fluids are also characterized by relatively high surface tensions as a result of their aryl substitution. In general, the polysiloxane fluids hereof will have a surface tension of at least about 24 dynes/cm², typically at least about 27 dynes/cm². Surface tension, for purposes hereof, is measured by a de Nouy ring tensiometer according to Dow Corning Corporate Test Method CTM 0461, Nov. 23, 1971. Changes in surface tension can be measured according to the above test method or according to ASTM Method D 1331.

Preferred high refractive index polysiloxane fluids have a combination of phenyl or phenyl derivative substituents (preferably phenyl), with alkyl substituents, preferably $C_1$–$C_4$ alkyl (most preferably methyl), hydroxy, $C_1$–$C_4$ alkylamino (especially —$R^1NHR^2NH2$ where each $R^1$ and $R^2$ independently is a $C_1$–$C_3$ alkyl, alkenyl, and/or alkoxy. High refractive index polysiloxanes are available from Dow Corning Corporation (Midland, Mich., U.S.A.) Huls America (Piscataway, N.J., U.S.A.), and General Electric Silicones (Waterford, N.Y., U.S.A;).

It is preferred to utilize high refractive index silicones in solution with a spreading agent, such as a silicone resin or a surfactant, to reduce the surface tension by a sufficient amount to enhance spreading and thereby enhance glossiness (subsequent to drying) of hair treated with the composition. In general, a sufficient amount of the spreading agent to reduce the surface tension of the high refractive index polysiloxane fluid by at least about 5%, preferably at least about 10%, more preferably at least about 15%, even more preferably at least about 20%, most preferably at least about 25%. Reductions in s tension of the polysiloxane fluid/spreading agent mixture can provide improved shine enhancement of the hair.

Also, the spreading agent will preferably reduce the surface tension by at least about 2 dynes/cm$^2$, preferably at least about 3 dynes/cm$^2$, even more preferably at least about 4 dynes/cm$^2$, most preferably at least about 5 dynes/cm$^2$.

The surface tension of the mixture of the polysiloxane fluid and the spreading agent, at the proportions present in the final product, is preferably 30 dynes/cm$^2$ or less, more preferably about 28 dynes/cm$^2$ or less most preferably about 25 dynes/cm$^2$ or less. Typically the surface tension will be in the range of from about 15 to about 30, more typically from about 18 to about 28, and most generally from about 20 to about 25 dynes/cm$^2$.

The weight ratio of the highly arylated polysiloxane fluid to the spreading agent will, in general, be between about 1000:1 and about 1:1, preferably between about 100:1 and about 2:1, more preferably between about 50:1 and about 2:1, most preferably from about 25:1 to about 2:1. When fluorinated surfactants are used, particularly high polysiloxane: spreading agent ratios may be effective due to the efficiency of these surfactants. Thus is contemplated that ratios significantly above 1000:1 may be used.

References disclosing examples of some suitable silicone fluids for use in the shampoo compositions include U.S. Pat. No. 2,826,551, U.S. Pat. No. 3,964,500, U.S. Pat. No. 4,364,837, British Pat. No. 849,433, and *Silicon Compounds*, Petrarch Systems, Inc. (1984), all of which art incorporated herein by reference.

Silicone resins can be included in the silicone conditioning agent. These resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Background material on silicones including sections discussing silicone fluids, guns, and resins, as well as manufacture of silicones, can be found in Encyclopedia of Polymer Science and Engineering, Volume 15, Second Edition, pp 204–308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadri- or tetrafunctional unit $SiO_2$. Primes of the unit symbols, e.g., M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T and/or Q' to D, D', M and/or M' in a silicone resin is indicative of higher levels of crosslinking. As discussed before, however, the overall level of crosslinking can also be indicated by the oxygen to silicon ratio.

The silicone resins for use herein which are preferred are MQ MT, MTQ, MDT and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

The weight ratio of the nonvolatile silicone fluid, having refractive curve index below 1.46, to the silicone resin component, when used, is preferably from about 4:1 to about 400:1, preferably this ratio is from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e. the conditioning active, the sum of the fluid and resin should be included in determining the level of silicone conditioning agent in the composition.

Optional Suspending Agent

The shampoo compositions of the present invention may further comprise a suspending agent at concentrations effective for suspending the optional silicone hair conditioning agent, or other water-insoluble material, in dispersed form in the shampoo compositions. Such concentrations range from about 0.1% to about 10%, preferably from about 0.3% to about 5.0%, by weight of the shampoo compositions.

Optional suspending agents include crystalline suspending agents that can be categorized as acyl derivatives, long chain amine oxides, or combinations thereof concentrations of which range from about 0.1% to about 5.0%, preferably from about 0.5% to about 3.0%, by weight of the shampoo compositions. When used in the shampoo compositions, these suspending agents are present in crystalline form. These suspending agents are described in U.S. Pat. No. 4,741,855, which description is incorporated herein by reference. These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having $C_8$–$C_{22}$ chains may be used.

Other long chain acyl derivatives suitable for use as suspending agents include N,N-dihydrocarbyl amido benzoic acid and soluble salts thereof (e.g., Na, K), particularly N,N-di(hydrogenated) $C_{16}$, $C_{18}$ and tallow amido benzoic acid species of this family, which are commercially available from Stepan Company (Northfield, Ill., USA).

Examples of suitable long chain amine oxides for use as suspending agents include alkyl ($C_{16}$–$C_{22}$) dimethyl amine oxides, e.g., stearyl dimethyl amine oxide.

Other suitable suspending agents include xanthan gum at concentrations ranging from about 0.3% to about 3%, preferably from about 0.4% to about 1.2%, by weight of the shampoo compositions. The use of xanthan gum as a suspending agent in silicone containing shampoo compositions is described, for example, in U.S. Pat. No. 4,788,006, which description is incorporated herein by reference. Combinations of long chain acyl derivatives and xanthan gum may also be used as a suspending agent in the shampoo compositions. Such combinations are described in U.S. Pat. No. 4,704,272, which description is incorporated herein by reference.

Other suitable suspending agents include carboxyvinyl polymers. Preferred among these polymers are the copolymers of acrylic acid crosslinked with polyallylsucrose as described in U.S. Pat. No. 2,798,053, which description is incorporated herein by reference. Examples of these polymers include Carbopol 934, 940, 941, and 956, available from B. F. Goodrich Company.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer.

Other suitable suspending agents may be used in the shampoo compositions, including those that can impart a gel-like viscosity to the composition, such as water soluble or colloidally water soluble polymers like cellulose ethers (e.g., methylcellulose, hydroxybutyl methylcellulose, hyroxypropylcellulose, hydroxypropyl methylcellulose, hydroxyethyl ethylcellulose and hydorxethylcellulose), guar gum, polyvinyl alcohol, polyvinyl pyrrolidone, hydroxypropyl guar gum, starch and starch derivatives, and other thickeners, viscosity modifiers, gelling agents, etc. Mixtures of these materials can also be used.

Method of Use

The shampoo compositions of the present invention are used in a conventional manner for cleansing and conditioning hair or skin. An effective amount of the composition for cleansing and conditioning the hair or skin is applied to the hair or skin, that has preferably been wetted with water, and then rinsed off. Such effective amounts generally range from about 1 gm to about 50 gm, preferably from about 1 gm to about 20 gm. Application to the hair typically includes working the composition through the hair such that most or all of the hair is contacted with the composition.

This method for cleansing and conditioning the hair or skin comprises the steps of:
a) wetting the hair or skin with water, b) applying an effective amount of the shampoo composition to the hair or skin , and c) rinsing the applied areas of the hair or skin with water. These steps can be repeated as many times as desired to achieve the desired cleansing and conditioning benefit.

EXAMPLES

The shampoo compositions illustrated in Examples I–XV illustrate specific embodiments of the shampoo compositions of the present invention, but are not intended to be limiting thereof. Other modifications can be undertaken by the skilled artisan without departing from the spirit and scope of this invention. These exemplified embodiments of the shampoo compositions of the present invention provide cleansing of hair and improved hair conditioning performance, and in particular provide improved wet hair conditioning in the form of improved wet hair feel during and after rinsing.

The shampoo compositions illustrated in Examples I–XV are prepared by conventional formulation and mixing methods, an examples of which is set forth hereinbelow. All exemplified amounts are listed as weight percents and exclude minor materials such as diluents, filler, and so forth, unless otherwise specified. The listed formulations, therefore, comprise the listed components and any minor materials associated with such components.

For each of the compositions illustrated in Examples I–XV, about one-third to all of the total alkyl sulfate surfactant is added to a jacketed mix tank and heated to about 74° C. with slow agitation to form a surfactant solution. Cationic polymer (Polyquat 10, cationic guar, etc.), insoluble liquid, polyalphaolefin, monosodium phosphate, disodium phosphate, EDTA, cocamide monoethanolamide and fatty alcohol, as applicable, are added to the tank and allowed to disperse. Ethylene glycol distearate (EGDS) is then added to the mixing vessel, and melted. After the EGDS is well dispersed (usually after about 5 to 20 minutes) optional preservative are added and mixed into the surfactant solution. This mixture is passed through a heat exchanger where it is cooled to about 35° C. and collected in a finishing tank. As a result of this cooling step, the ethylene glycol distearate crystallizes to form a crystalline network in the product. The remainder of the ammonium laureth sulfate, lauryl sulfate and other ingredients including a silicone premix (described hereinafter), if applicable, are added to the finishing tank with ample agitation to insure a homogeneous mixture. A sufficient amount of the silicone premix is added to provide the desired level of dimethicone in the final product. Once all ingredients have been added, ammonium xylene sulfonate or additional sodium chloride can be added to the mixture to thin or thicken respectively to achieve a desired product viscosity. Preferred viscosities range from about 3500 to about 9000 centistokes at 25° C. (as measured by a Wells-Brookfield cone and plate viscometer at 2/s at 3 minutes).

When silicone hair conditioning oils are used, a silicone premix is prepared by adding 70% dimethicone, 29% ammonium laureth-3 sulfate (solution basis, 26% active) and 1% sodium chloride, all by weight of the silicone premix to a high shear mixing vessel and mixing for about 30 minutes or until the desired silicone particle size is achieved (typically a number average particle size of from about 5 microns to about 25 microns). A conventional silicone emulsion may also be used.

| Component | Example Number | | | | |
|---|---|---|---|---|---|
| | I | II | III | IV | V |
| Ammonium laureth-3 sulfate | 10 | 10 | 12.0 | 10.0 | 10.0 |
| Ammonium lauryl sulfate | 10 | 6.0 | 4.0 | 6.0 | 6.0 |
| Cocamide MEA | 1.45 | 0.85 | 0.68 | 0.8 | 0.8 |
| Polyquat 10[1] | 0.2 | 0 | 0.4 | 0 | 0.15 |
| Guar hydroxypropyltrimonium chloride 2 | 0 | 0.2 | 0 | 0.15 | 0 |
| Hydrogenated Polyalpha Olefin[3] | 0.4 | 0.32 | 0.25 | 0.4 | 0.3 |
| Cetyl alcohol | 0.42 | 0 | 0.42 | 0.6 | 0.42 |
| Stearyl alcohol | 0.18 | 0 | 0.18 | 0 | 0.18 |
| Ethylene glycol distearate | 1.5 | 2.0 | 1.5 | 1.5 | 2.0 |
| Dimethicone[4] | 2.0 | 1.0 | 0 | 0 | 1.5 |
| Monosodium phosphate | 0.1 | 0.1 | 0.1 | 0 | 0 |
| Disodium phosphate | 0.2 | 0.2 | 0.2 | 0 | 0 |
| EDTA | 0.1 | 0.1 | 0.1 | 0.1 | 0.1 |
| Perfume solution | 0.45 | 0.45 | 0.6 | 0.6 | 0.6 |
| DMDM hydantoin | 0.37 | 0.37 | 0.37 | 0.37 | 0.37 |
| Color solution (ppm) | 64 | 64 | 64 | 64 | 64 |
| Water and minors | q. s. to 100% | | | | |

| Component | Example Number | | | | |
|---|---|---|---|---|---|
| | VI | VII | VIII | IX | X |
| Ammonium laureth-3 sulfate | 10 | 10 | 12.0 | 10.0 | 10.0 |
| Ammonium lauryl sulfate | 10 | 6.0 | 4.0 | 6.0 | 6.0 |
| Cocamide MEA | 0 | 0.85 | 0.68 | 0 | 0 |
| Cocamide DEA | 1.4 | 0 | 0 | 0.8 | 0.0 |
| Polyquat 10[5] | 0.2 | 0 | 0.2 | 0.5 | 0.15 |
| Guar hydroxypropyltrimonium chloride[6] | 0 | 0.2 | 0 | 0 | 0 |
| Hydrogenated Polyalpha Olefin[3] | 0.4 | 0.32 | 0.25 | 0.4 | 0.3 |
| Cetyl alcohol | 0.42 | 0 | 0.42 | 0.6 | 0.42 |
| Stearyl alcohol | 0.18 | 0 | 0.18 | 0 | 0.18 |
| Ethylene glycol distearate | 1.5 | 1.5 | 1.5 | 1.5 | 2.0 |
| Dimethicone[4] | 2.5 | 0.5 | 0 | 2.0 | 0.5 |
| Monosodium phosphate | 0.1 | 0.1 | 0.1 | 0.1 | 0 |
| Disodium phosphate | 0.2 | 0.2 | 0.2 | 0.2 | 0 |
| EDTA | 0.1 | 0.1 | 0.1 | 0.1 | 0.1 |
| Perfume solution | 0.45 | 0.45 | 0.6 | 0.6 | 0.6 |
| DMDM hydantoin | 0.37 | 0.37 | 0.37 | 0.37 | 0.37 |
| Color solution (ppm) | 64 | 64 | 64 | 64 | 64 |
| Water and minors | q. s. to 100% | | | | |

| Component | Example Number | | | | |
|---|---|---|---|---|---|
| | XI | XII | XIII | XIV | XV |
| Ammonium laureth-3 sulfate | 10 | 10 | 12.0 | 10.0 | 10.0 |
| Ammonium lauryl sulfate | 10 | 6.0 | 4.0 | 6.0 | 6.0 |
| Cocamide MEA | 0 | 0.85 | 0.68 | 0 | 0 |
| Cocamide DEA | 1.4 | 0 | 0 | 0.8 | 0.0 |
| Polyquat 10[5] | 0.2 | 0 | 0.4 | 0.5 | 0.15 |
| Guar hydroxypropyltrimonium chloride[6] | 0 | 0.2 | 0 | 0 | 0 |
| Polyalpha olefin[7] | 0.4 | 0.32 | 0.25 | 0.4 | 0.3 |
| Cetyl alcohol | 0.42 | 0 | 0.42 | 0.6 | 0.42 |
| Stearyl alcohol | 0.18 | 0 | 0.18 | 0 | 0.18 |
| Ethylene glycol distearate | 1.5 | 1.5 | 1.5 | 1.5 | 2.0 |
| Dimethicone[4] | 2.5 | 0.5 | 0 | 2.0 | 0.5 |
| Monosodium phosphate | 0.1 | 0.1 | 0.1 | 0.1 | 0 |
| Disodium phosphate | 0.2 | 0.2 | 0.2 | 0.2 | 0 |
| EDTA | 0.1 | 0.1 | 0.1 | 0.1 | 0.1 |
| Perfume solution | 0.45 | 0.45 | 0.6 | 0.6 | 0.6 |
| DMDM hydantoin | 0.37 | 0.37 | 0.37 | 0.37 | 0.37 |
| Color solution (ppm) | 64 | 64 | 64 | 64 | 64 |
| Water and minors | q. s. to 100% | | | | |

[1]. JR 30M available from Amerchol
[2]. Jaguar C-17 available from Rhone-Poulenc
[3]. SHF 62 available from Mobil Chemical
[4]. Dimethicone is a 40(gum)/60(fluid) weight ratio blend of SE-76 dimethicone gum available from General Electric Silicones Division and a dimethicone fluid having a viscosity of 350 centistokes.
[5]. LR 400 available from Amerchol
[6]. N-Hance 3196 available from Aqualon
[7]. SHF 21 available from Mobil Chemical

What is claimed is:

1. A conditioning shampoo composition comprising:

(A) from about 5% to about 50% by weight of a detersive surfactant component selected from the group consisting of anionic surfactants, zwitterionic or amphoteric surfactants having an attached group that is anionic at the pH of the composition, and combinations thereof;

(B) from about 0.5% to about 3% by weight of an organic, cationic, hair conditioning polymer having a cationic charge density of from about 0.2 meq/gm to about 7 meq/gm and a molecular weight of from about 5,000 to about 10 million;

(C) from about 0.25% to about 3% by weight of an organic, water-insoluble, polyalphaolefin polymer derived from 1-alkene monomers from 8 to 12 carbon atoms, wherein the polyalphaolefin has a viscosity of from about 1 to about 50 centipoise as measured at 40° C.; and (D) from about 20% to about 94% by weight of water.

2. The shampoo composition of claim 1 wherein the viscosity of the polyalphaolefin is from about 2 to about 50 centipoise.

3. The shampoo composition of claim 1 wherein the composition comprises from about 0.5% to about 2% by weight of the organic, cationic, hair conditioning polymer.

4. The shampoo composition of claim 1 wherein the composition comprises from about 0.4% to about 1.5% by weight of the polyalphaolefin.

5. The shampoo composition of claim 4 wherein the composition comprises from about 0.4% to about 1% by weight of the polyalphaolefin.

6. The shampoo composition of claim 1 wherein the detersive surfactant component comprises from about 8% to about 30% by weight of alkyl sulfate, alkyl ether sulfate, or combination thereof.

7. A conditioning shampoo composition comprising:

(A) from about 8% to about 30% by weight of a detersive surfactant component selected from the group consisting of anionic surfactants, zwitterionic or amphoteric surfactants having an attached group that is anionic at the pH of the composition, and combinations thereof;

(B) from about 0.5% to about 3% by weight of an organic, cationic, hair conditioning polymer having a cationic charge density of from about 0.2 meq/gm to about 7 meq/gm and an average molecular weight of from about 5,000 to about 10 million;

(C) from about 0.01% to about 10% by weight of an insoluble, non volatile, silicone, hair conditioning agent;

(D) from about 0.25% to about 3% by weight of an organic, water-insoluble, polyalphaolefin polymer derived from 1-alkene monomers from 8 to 12 carbon atoms, wherein the polyalphaolefin has a viscosity of from about 1 to about 50 centipoise as measured at 40° C.; and (E) from about 20% to about 94% by weight of water.

8. The shampoo composition of claim 7 wherein the viscosity of the polyalphaolefin is from about 2 to about 50 centipoise.

9. The shampoo composition of claim 7 wherein the composition comprises from about 0.5% to about 2% by weight of the organic, canonic, hair conditioning polymer.

10. The shampoo composition of claim 7 wherein the composition comprises from about 0.4% to about 1.5% by weight of the polyalphaolefin.

11. The shampoo composition of claim 7 wherein the composition comprises from about 0.4% to about 1% by weight of the polyalphaolefin.

12. The shampoo composition of claim 7 wherein the detersive surfactant component comprises alkyl sulfate, alkyl ether sulfate, or combinations thereof.

13. The shampoo composition of claim 1, further comprising from about 0.001% to about 20%, by weight, of an anti-dandruff agent.

* * * * *